United States Patent
Currie et al.

(10) Patent No.: US 7,034,059 B2
(45) Date of Patent: Apr. 25, 2006

(54) METHODS OF USING NORFLUOXETINE

(75) Inventors: Mark G. Currie, Sterling, MA (US);
Steven W. Jones, Milford, MA (US);
Chrisantha H. Senanayake,
Shrewsbury, MA (US); Zhi-Hiu Lu,
Shrewsbury, MA (US)

(73) Assignee: Sepracor Inc., Marlborough, MA (US)

( * ) Notice: Subject to any disclaimer, the term of this patent is extended or adjusted under 35 U.S.C. 154(b) by 181 days.

(21) Appl. No.: 10/183,472

(22) Filed: Jun. 28, 2002

(65) Prior Publication Data

US 2003/0096019 A1    May 22, 2003

Related U.S. Application Data

(60) Provisional application No. 60/301,847, filed on Jul. 2, 2001.

(51) Int. Cl.
*A61K 31/135* (2006.01)
(52) U.S. Cl. .................................................... 514/649
(58) Field of Classification Search ................. 514/649
See application file for complete search history.

(56) References Cited

U.S. PATENT DOCUMENTS

| | | | |
|---|---|---|---|
| 3,155,669 A | 11/1964 | Adriaan et al. |
| 3,155,670 A | 11/1964 | Adriaan et al. |
| 3,466,325 A | 9/1969 | Brandstrom et al. |
| 3,471,515 A | 10/1969 | Troxler et al. |
| 3,536,809 A | 10/1970 | Applezweig |
| 3,551,493 A | 12/1970 | Ruschig et al. |
| 3,598,123 A | 8/1971 | Zaffaroni |
| 3,630,200 A | 12/1971 | Higuchi |
| 3,845,770 A | 11/1974 | Theeuwes et al. |
| 3,916,899 A | 11/1975 | Theeuwes et al. |
| 3,960,891 A | 6/1976 | Malen et al. |
| 4,008,719 A | 2/1977 | Theeuwes et al. |
| 4,018,895 A | 4/1977 | Molloy et al. |
| 4,035,511 A | 7/1977 | Messing et al. |
| 4,194,009 A | 3/1980 | Molloy et al. |
| 4,207,343 A | 6/1980 | Lavagnino et al. |
| 4,313,896 A | 2/1982 | Molloy et al. |
| 4,314,081 A | 2/1982 | Molloy et al. |
| 4,329,356 A | 5/1982 | Holland |
| 4,444,778 A | 4/1984 | Coughlin |
| 4,584,404 A | 4/1986 | Molloy et al. |
| 4,590,213 A | 5/1986 | Stark |
| 4,594,358 A | 6/1986 | Hynes |

(Continued)

FOREIGN PATENT DOCUMENTS

EP    0 294 028 A2    11/1988

(Continued)

OTHER PUBLICATIONS

Paul, Fundamental Immunology, 3rd ed., 1993, p. 1015-1032.*

(Continued)

*Primary Examiner*—San-Ming Hui
(74) *Attorney, Agent, or Firm*—Jones Day

(57) ABSTRACT

The invention encompasses methods of using racemic and enantiomerically pure norfluoxetine, as well as pharmaceutical compositions, pharmaceutical unit dosage forms, and kits comprising racemic and enantiomerically pure norfluoxetine. In particular, the invention encompasses a method of inhibiting or reducing the production of $PGE_2$. The invention further encompasses a method of treating or preventing inflammation in a patient, as well as a method of treating or preventing a disease or disorder such as, but not limited to, autoimmune diseases, arthritis, neurologic diseases, inflammatory diseases, fibromyalgia, pain resulting from inflammation, neuropathic pain, and cancer.

14 Claims, 2 Drawing Sheets

U.S. PATENT DOCUMENTS

Figure 1:
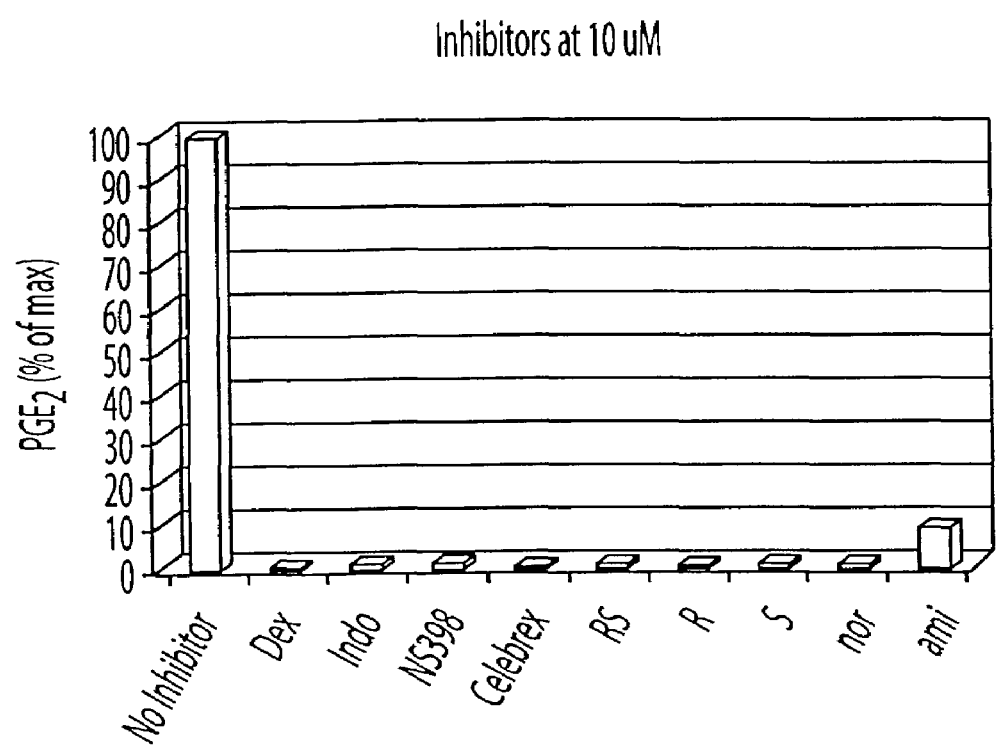

| | | |
|---|---|---|
| 4,596,807 A | 6/1986 | Crosby |
| 4,626,549 A | 12/1986 | Molloy et al. |
| 4,647,591 A | 3/1987 | Cherkin et al. |
| 4,683,235 A | 7/1987 | Hynes |
| 4,698,342 A | 10/1987 | Crosby |
| 4,710,500 A | 12/1987 | Perregaard |
| 4,777,173 A | 10/1988 | Shrotryia et al. |
| 4,797,286 A | 1/1989 | Thakker et al. |
| 4,831,031 A | 5/1989 | Lowe, III et al. |
| 4,847,092 A | 7/1989 | Thakker et al. |
| 4,868,344 A | 9/1989 | Brown |
| 4,895,845 A | 1/1990 | Seed |
| 4,918,207 A | 4/1990 | Brown |
| 4,918,242 A | 4/1990 | Brown |
| 4,918,246 A | 4/1990 | Brown |
| 4,940,585 A | 7/1990 | Hapworth et al. |
| 4,950,791 A | 8/1990 | Brown |
| 4,971,998 A | 11/1990 | Wurtman et al. |
| 4,988,814 A | 1/1991 | Abou-Gharbia et al. |
| 5,104,899 A | 4/1992 | Young et al. |
| 5,114,976 A | 5/1992 | Norden |
| 5,250,571 A | 10/1993 | Fuller et al. |
| 5,356,934 A | 10/1994 | Robertson et al. |
| 5,512,593 A | 4/1996 | Dante |
| 5,527,788 A | 6/1996 | Svec et al. |
| 5,532,268 A | 7/1996 | Wong et al. |
| 5,538,992 A | 7/1996 | Wong et al. |
| 5,552,429 A | 9/1996 | Wong et al. |
| 5,589,511 A | 12/1996 | Young et al. |
| 5,648,396 A | 7/1997 | Young et al. |
| 5,708,035 A | 1/1998 | Young et al. |
| 5,747,494 A | 5/1998 | Medjad et al. |

FOREIGN PATENT DOCUMENTS

| | | |
|---|---|---|
| EP | 0 369 685 A1 | 5/1990 |
| EP | 0 444 855 | 9/1991 |
| EP | 0 449 561 A2 | 10/1991 |
| EP | 0 687 472 A2 | 10/1994 |
| EP | 0 722 941 A2 | 7/1996 |
| EP | 0 759 299 A1 | 2/1997 |
| EP | 0 792 649 A1 | 9/1997 |
| EP | 0 830 864 A1 | 3/1998 |
| WO | WO 89/03692 | 5/1989 |
| WO | WO 92/00103 | 1/1992 |
| WO | WO 95/28152 | 10/1995 |
| WO | WO 96/09044 | 3/1996 |
| WO | WO 96/09047 | 3/1996 |
| WO | WO 96/33710 | 10/1996 |
| WO | WO 97/31629 | 9/1997 |
| WO | WO 99/61014 | 12/1999 |

OTHER PUBLICATIONS

Bianchi et al., Inflamm. Res., 1995;44:466-469.*
Al-Haboudi et al., Eur. J. Pharmacolo., 1982;78(2):175-185, abstract.*
Aleve monograph in PDR 51st ed., 1997, p. 2124.*
Adly et al., "Fluoxetine Prophylaxis of Migraine," Headache 32: 101-104 (1992).
Arvanitis, et al., 1997, "Multiple fixed doses of seroquel (Quetiapine) in patients with acute exacerbation of schizophrenia: a comparison with Haloperidol and placebo", Biol. Psychiatry 15:233-246.
Aspeslet et al., "The Effects of Desipramine and Iprindole on Levels of Enantiomers of Fluoxetine in Rat Brain and Urine," Chirality, 6:86-90 (1994).
Bach et al., "Ritanserin as Adjunct to Fluoxetin Treatment of OCD Patients with Psychotic Features," Pharmacopsychiatry, 30(1):28-29 (1997).

Benfield et al., "Fluoxetine: A Review of Its Pharmacodynamic and Pharmacokinetic Properties, and Therapeutic Efficacy in Depressive Illness", Drugs 32: 481-508 (1986).
Bergstrom et al., "Quantification and Mechanism of the Fluoxetine and Tricyclic Antidepressant Interaction," Clin. Pharmacol. Ther. 51: 239-248 (1992).
Bremner, "Fluoxetine in Depressed Patients: A Comparison with Imipramine", J. Clin. Psychiatry, 45(10): 414-420 (1984).
Brown et al., 1998, "Sertindole, a new atypical antipsychotic for the treatment of schizophrenia", Pharmacotherapy, 18(1):69-83.
Caccia et al., "Influence of Dose and Route of Administration on the Kinetics of Fluoxetine and Its Metabolite Norfluoxetine in the Rat", Psychopharmacology, 100: 509-514 (1990).
Cliffe et al., 1993, "(S)-N-tert-Butyl-3-(4-(2-methoxyphenyl)-piperazin-1-yl)-2-phenylpropanamide [(S)-WAY-100135]: A Selective Antagonist at Presynaptic and Postsynaptic 5-HT$_{1A}$ Receptors", J. Med. Chem. 36:1509-1510.
Corey and Reichard, "Enantioselective and Practical Syntheses of R- and S-Fluoxetines", Tetrahedron Lett., 30(39): 5207-5210 (1989.
Coutts and Baker, "Implications of Chirality and Geometric Isomerism in Some Psychoactive Drugs and Their Metabolites", Chirality, 1: 99-120 (1989).
Coutts and Baker, "Metabolic Implications of Chiral Centres in Psychotropic Drugs", Prog. Neuro-Psychopharmacol. & Biol. Psychiat., 13: 405-417 (1989).
Davis and Markham, 1997, "Ziprasidone", CNS Drugs, 8(2):153-159.
Dreshfield et al., 1996, "Enhancement of Fluoxetine-Dependent Increase of Extracellular Serotonin (5-HT) Levels by (-)- Pindolol, an Antagonist at 5-HT$_{1A}$ Receptors", Neurochem. Res. 21(5):557-562.
Faustman et al., 1996, "Effects of 'Seroquel' (Quetiapine) on platelet serotonin-2 binding in schizophrenia", J. Clin. Psychopharmacol. 16:464-466.
Fleischhacker et al., 1997, "Drug treatments of schizophrenia in the 1990s", Drugs 53:915-929.
Fuller and Snoddy, "Fluoxetine Enantiomers as Antagonists of p-Chloroamphetamine Effects in Rats", Pharmacology Biochemistry & Behavior, 24: 281-284 (1986).
Fuller et al., "Comparison of Fluoxetine and Norfluoxetine Enantiomers as Inhibitors of Hexobarbitone Metabolism in Mice," J. Pharm. Pharmacol., 44(12):1041-1042 (1992).
Gao and Sharpless, "Asymmetric Synthesis of Both Enantiomers of Tomoxetine and Fluoxetine. Selective Reduction of 2,3-Epoxycinnamyl Alcohol with Red-A1", J. Org. Chem., 53(17): 4081-4084 (1988).
Goodman & Gilman, The Pharmacological Basis of Therapeutics, 9th Ed. McGraw-Hill, 1996, pp. 363, 404.
Hillver et al., 1990, "(S)-5-Fluoro-8-hydroxy-2-(dipropylamino)tetralin: A Putative 5-HT$_{1A}$-Receptor Antagonist", J. Med. Chem. 33:1541-1544.
Jamali et al., "Enantioselective Aspects of Drug Action and Disposition: Therapeutic Pitfalls", J. Pharm. Sci. 78(9): 695-715. (1989).
Kim and Wurtman, "Selective Effects of CGS 10686B, d1-Fenfluramine or Fluoxetine on Nutrient Selection", Physiology & Behavior, 42: 319-322 (1988).
Lacombe, 1993, "Pharmacological profile of Risperidone", Can. J. Psychiatry 38 Suppl.:S80 -S88.

Medical Sciences Bulletin, 1997, "Quetiapine approved for management of psychotic disorders", Issue No. 241.

Megens et al., "In Vivo Pharmacological Profile of 9-Hydroxyrisperidone, the Major Metabolite of the Novel Antipsychotic Risperidone," *Drug Development Research*, 33(4):399-412 (1994).

*The Merck Index*, 1996, 12th Ed., Merck & Co., Inc., Whitehouse Station, NJ, pp. 1455, 1737.

Middlemiss et al., 1992, "Centrally Active 5-HT Receptor Agonists and Antagonists", Neurosci. and Biobehav. Rev. 16:75-82

Misra et al., "Quetiapine: A New A typical Antipsychotic," *South Dakota Journal of Medicine*, 51(6):189-193 (1998).

Moreau et al., 1992, "Behavioral Profile of the $5HT_{1A}$ Receptor Antagonist (S)-UH-301 in Rodents and Monkeys", Brain Res. Bull. 29:901-904.

Olesen et al., "Serum Concentrations and Side Effects in Psychiatric Patients During Risperidone Therapy," *Therapeutic Drug Monitoring*, 1380-1384 (1998).

Physician's Desk Reference, 51st Edition, 1997, pp. 2428-2429, 2547-2548, 2832-2834.

Physician's Desk Reference, 52 Edition, 1998, pp. 130, 470-473, 725-726, 782, 859-860, 976-978, 1227, 1309-1310, 1396, 1512, 1834, 1894, 1997-1998, 2164, 2275-2276, 2294-2295, 2475, 2494-2495, 2512-2513, 2520, 2522-2523, 2527, 2666, 2862, 2870-2871, 2958-2959, 3013, 3132.

Physicians Desk Reference, pp. 905-908, 44th Ed., Medical Economics Data Production Co., N.J. (1990).

Power-Smith, "Beneficial Sexual Side-effects from Fluoxetine," *Brit. J. Psychiatry* 164: 249-250 (1994).

Robertson et al., "Absolute Configurations and Pharmacological Activities of the Optical Isomers of Fluoxetine, a Selective Serotonin-Uptake Inhibitor", *J. Med. Chem.*, 31(7): 1412-1417 (1988).

Saper et al., "Double-Blind Trial of Fluoxetine: Chronic Daily Headache and Migraine," *Headache* 34: 497-502 (1994).

Saxena et al., "Risperidone Augmentation of SRI Treatment for Refractory Obsessive-Compulsive Disorder," *Journal of Clinical Psychiatry*, 57(7):303-306 (1996).

Schmider et al., "Inhibition of CYP2C9 by Selective Serotonin Reuptake Inhibitors In Vitro: Studies of Phenytoin p-Hydroxylation," *Br. J. Clin. Pharmacol.*, 44(5):495-498 (1997).

Scrip's New Product Review, No. 7, pp. 13-14 (1986).

Small et al., 1997, "Quetiapine in patients with schizophrenia", Arch. Gen. Psychiatry, 54:549-557.

Stevens et al., "Interaction of the Enantiomers of Fluoxetine and Norfluoxetine with Human Liver Cytochromes P450," *J. Pharmacology & Experimental Therapeutics* 226(7): 964-971 (1993).

Teicher et al., "Emergence of Intense Suicidal Preoccupation During Fluoxetine Treatment", *Am. J. Psychiatry*, 147(2): 207-210 (1990).

Wong et al., "Affinities of Fluoxetine, Its Enantiomers, and Other Inhibitors of Serotonin Uptake for Subtypes of Serotonin Receptors", *Neuropsychopharm*, 5(1):43-47 (1991).

Wong et al., "Fluoxetine and Its Two Enantiomers as Selective Serotonin Uptake Inhibitors", *Acta Pharm. Nord.*, 2(3): 171-180 (1990).

Wong et al., "Inhibition of Serotonin Uptake by Optical Isomers of Fluoxetine", *Drug Development Research*, 6: 397-403 (1985).

Wong et al., "Suppression of Food Intake in Rats by Fluoxetine: Comparison of Enantiomers and Effects of Serotonin Antagonists", *Pharmacology Biochemistry & Behavior*, 31: 475-479 (1988).

* cited by examiner

METHODS OF USING NORFLUOXETINE

This application claims priority to U.S. provisional patent application No. 60/301,847, filed Jul. 2, 2001, the entirety of which is incorporated herein by reference.

1. FIELD OF THE INVENTION

This invention relates to pharmaceutical compositions comprising enantiomerically pure R- or S-norfluoxetine, and methods of using enantiomerically pure R- or S-norfluoxetine for the treatment or prevention of inflammation and related disorders.

2. BACKGROUND OF THE INVENTION

2.1. Inflammation

Inflammation can be elicited by a variety of stimuli. Examples include infectious agents, ischemia, antigen-antibody interactions, and thermal or other physical injury. *Goodman and Gilman's The Pharmcological Basis of Therapeutics* 617–618 ($9^{th}$ ed.; 1996). Consequently, inflammation is associated with a large number of diseases and conditions.

For example, the inflammation of connective tissue is characteristic of diseases and disorders such as rheumatoid arthritis, tendinitis, and tenosynovitis, which affect tens of thousands of people each year. *Merck Manual* 416–422, 455, 479–481 ($17^{th}$ ed.; 1999). Other examples of inflammation include chronic inflammation of the gastrointestinal tract, which is characteristic of diseases such as Crohn's disease and ulcerative colitis (id. at 302); inflammation of nerve tissue, which is characteristic of neuropathies such as Guillain-Barré syndrome, (id. at 1494–1495); and inflammation of blood vessels, which is characteristic of vasculitis (e.g., Henoch-Schönlein syndrome, or *Pseudomonas septicemia* or drug-induced vasculitis, erythema nodosum, polyarteritis nodosa, temporal arteritis, and Takayasu's arteritis). Id. at 437–442. A significant number of people also suffer from systemic inflammation, which is typical of diseases such as Sjögren's Disorder, Behcet's Syndrom, relapsing polychondritis, systemic lupus erythematosus, eosinophilic fasciitis, polymyositis, and dermatomyositis. Id. at 423–436. Other examples and types of inflammation are well known to the medical community.

A variety of drugs can be used to treat inflammation, some of which work better than others, and some of which exhibit fewer or less severe adverse effects than others. But the safety and effectiveness of a particular anti-inflammatory drug can depend on a variety of factors, including its mechanism of action.

The inflammatory process is a complex and varied one. For example, several classes of leukocytes reportedly play essential roles in inflammation, as do various molecules that adhere leukocytes to sites of inflammation. It has been suggested that non-steroidal anti-inflammatory drugs (NSAIDs) act by inhibiting the expression or activity of certain adhesion molecules, although the principle effects of NSAIDs are reportedly due to their inhibition of prostaglandin biosynthesis. *Goodman and Gilman's The Pharmcological Basis of Therapeutics* 618, 620–622 ($9^{th}$ ed.; 1996). A large number of soluble mediators (e.g., histamine) also appear to be involved in the inflammation process, as do several different cytokines such as Interleukin 1 (IL-1) and Tumor Necrosis Factor (TNF). Id. Other cytokines and growth factors that may be involved in the process include IL-2, IL-6, IL-8, and GM-CSF. Peptides that promote firing of pain fibers, such as Substance P, have also been implicated in the process. Id. at 619. In addition to these and the myriad of other compounds, processes, and interactions associated with inflammation, is has been suggested that bradykinin and 5-hydroxytryptamine (serotonin, 5-HT) may play a role in mediating certain types of inflammation. Id.

Because inflammation is a symptom common to so many diseases and disorders, there remains a need for new anti-inflammatory and analgesic drugs. A particular need exists for anti-inflammatory drugs that operate more effectively or incur fewer adverse effects than those currently available. For example, NSAIDs can cause the formation of gastric or intestinal ulcerations, can inhibit platelet aggregation, and can promote the retention of salt and water, thereby reducing the effectiveness of antihypertensive regimes. Id. at 622–623.

It is also desirable to provide new anti-inflammatory drugs that incur fewer or different adverse drug-drug interactions than those which are currently available. For example, when NSAIDs are administered with diuretics such as hydrochlorothiazide, they can increase the risk of renal failure. See, e.g., *Physicians' Desk Reference* 3287 ($54^{th}$ ed.; 2000). NSAIDs such as ketoprofen can also affect the elimination of certain drugs (e.g., methotrexate), leading to elevated serum levels of those drugs and increasing their toxicity. Id. See also, *Goodman and Gilman's The Pharmcological Basis of Therapeutics* 624–625 ($9^{th}$ ed.; 1996).

Perhaps for these reasons, researchers have investigated whether drugs typically not associated with the treatment of inflammation can affect it. For example, it has been reported that certain psychotropic agents inhibit the conversion of arachidonic acid to Prostaglandin $E_2$ ($PGE_2$) in vitro. Krupp, P., and West, M. *Experientia* 31:330–331 (1975). It has also been reported that certain tricyclic antidepressants and methyl xanthine compounds behave as prostaglandin antagonists in vitro. Horrobin, D. F., and Manku, M. S., *Med. Hypothesis* 3:71–86 (1977). Studies done with rats, however, have suggested alternative mechanisms by which specific anti-depressants may affect pain and inflammation. See, e.g., El-Mahdy, S. A. M., et al., *J. Pharm. Pharmacol.* 42:522–524 (1990). See also, Michelson, D., et al., *Agents Actions* 42:25–28 (1994); Butler, S. H., et al., *Pain* 23:159–175 (1985); Bianci, M., et al., *Eur. J. Pharmacol.* 219:113–116 (1992); Martelli, E. A., et al., *Eur. J. Pharmacol.* 2:229–233 (1967);

Research has shown quite clearly that different drugs act in different ways. For example, tricyclic antidepressants reportedly affect polymorphonuclear cell (PMN) migration, an activity associated with the recruitment of leukocytes to loci of inflammation or infection. Sacerdote, P., et al., *Gen. Pharmac.* 25(3):409–412 (1994). However, the anti-depressant fluoxetine reportedly does not affect PMN migration. Id. at 411. The different activities of fluoxetine and tricyclic antidepressants has also been reported by Bianchi and coworkers. See, e.g., Bianchi, M., and Panerai, A. E., *Pharmacol. Res.* 33(4/5):235–238 (1996). Further research has shown that the antinociceptive action of tricyclic antidepressants is independent of the anti-depressant effect. See, e.g., Bianchi, M., et al., *Pharm. Biochem. Behav.* 48(4): 1037–1040 (1994). It has also been reported that the effects that anti-depressants have on mechanisms associated with pain and inflammation vary between species. See, e.g., Ventafridda, V., et al., *Pain* 43:155–162 (1990). For example, drugs can affect rats and humans differently. Id.

2.2. Fluoxetine and Norfluoxetine

Fluoxetine, which is chemically named (±)-N-methyl-γ-[4-(trifluoromethyl)-phenoxy]benzenepropanamine, is an anti-depressant that is sold under the trade name Prozac®. *Physicians' Desk Reference* 962–966 (54$^{th}$ ed.; 2000). See also U.S. Pat. Nos. 4,018,895 and 4,194,009, each of which is incorporated herein by reference.

Although racemic fluoxetine is approved as being safe and effective only for the treatment of depression in the United States, its effect on other diseases and conditions has been investigated. One example is fibromyalgia. Goldenberg, D., et al., *Arthritis & Rheumatism* 39(11):1852–1859 (1996). Reports also suggest that racemic fluoxetine can affect inflammatory edema in the paws of rats, as well as subcutaneous carrageenin-induced inflammation in rats. Bianchi, M., et al., *Eur. J. Pharmacol.* 263:81–84 (1994); Bianchi, M., et al., *Inflamm. Res.* 44:466–469 (1995). However, the mechanism by which racemic fluoxetine acts to reduce inflammation in rats remains unclear. See, e.g., Yaron, I., et al., *Arthritis & Rheumatism* 42(12):2561–2568 (1999). It has also been reported that the combined administration of racemic fluoxetine and codeine or dextropropoxyphene can be used to treat pain. See U.S. Pat. Nos. 4,683,235 and 4,594,358 and European Patent Application 0193355.

Fluoxetine is commercially available as a racemic compound. It has been reported, however, that enantiomerically pure enantiomers of fluoxetine (i.e., R(−)-fluoxetine and S(+)-fluoxetine) are reportedly useful in the treatment of depression and other conditions, such as pain, in humans. See, e.g., U.S. Pat. Nos. 5,708,035, 5,648,396, and 5,589,511.

The primary metabolite of fluoxetine in humans in norfluoxetine, which is described in U.S. Pat. No. 4,313,896 and European Patent Application 0 369 685. Norfluoxetine, which is chemically named (±)-γ-[4-(trifluoromethyl)-phenoxy]benzenepropanamine, is a racemic mixture of two enantiomers, R-norfluoxetine and S-norfluoxetine, the structures of which are shown below:

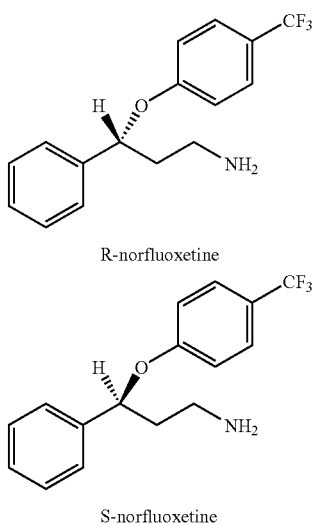

R-norfluoxetine

S-norfluoxetine

It has been reported that racemic norfluoxetine can be used in the treatment of disorders such as depression, abnormal muscular function, abnormal pituitary function, inability to sleep, abnormal sexual performance, and abnormal appetite (U.S. Pat. No. 4,313,896), hypertension (U.S. Pat. No. 4,329,356), atherosclerosis (U.S. Pat. No. 4,444,178), anxiety (U.S. Pat. No. 4,590,213), weight gain (U.S. Pat. No. 4,895,845), and diabetes (EPA 0 294 028). Some animal studies have also suggested that racemic fluoxetine has analgesic activity. Benfield, P., et al., *Drugs* 32:481–508, 489 (1986); Robertson, D. W., et al., *J. Med. Chem.* 31:1412–1417 (1988). It has also been reported that the combined administration of racemic norfluoxetine and codeine or dextropropoxyphene can be used to treat pain. See U.S. Pat. Nos. 4,683,235 and 4,594,358 and European Patent Application 0193355.

Although uses have been suggested for racemic norfluoxetine, only the S-enantiomer exhibits the potent and selective serotonin uptake inhibition of its racemic parent. R-norfluoxetine is significantly less potent than racemic fluoxetine in inhibiting serotonin uptake. *Physicians' Desk Reference* 962 (54$^{th}$ ed.; 2000).

3. SUMMARY OF THE INVENTION

This invention is based, in part, on the unexpected discovery that metabolites of serotonin reuptake inhibitors can exhibit anti-inflammatory activity, and can be used in the treatment or prevention of a large number of diseases and disorders. The invention encompasses methods of treating or preventing disease and disorders which include, but are not limited to, inflammation, autoimmune diseases (e.g., lupus erythematosus and multiple sclerosis), arthritis (e.g., rheumatoid arthritis and osteoarthritis), neurologic diseases (e.g., Alzheimer's dementia, amyotrophic lateral sclerosis and Parkinson's disease), inflammatory diseases (e.g., sepsis, adult respiratory distress syndrome, inflammatory bowel disease, and disseminated intravascular coagulation), fibromyalgia, pain resulting from inflammation (e.g., hyperalgesia and allodynia), neuropathic pain, and cancer (e.g., colon cancer and rectal cancer).

Each of the methods of the invention comprises administering to a patient in need of such treatment or prevention a therapeutically or prophylactically effective amount of norfluoxetine, or a pharmaceutically acceptable salt, solvate, hydrate, or clathrate thereof. Preferred methods comprise the administration of an enantiomerically pure enantiomer of norfluoxetine, or a pharmaceutically acceptable salt, solvate, hydrate, or clathrate thereof. In particularly preferred methods, the enantiomer of norfluoxetine is R-norfluoxetine.

The invention further encompasses pharmaceutical compositions and pharmaceutical unit dosage forms that comprise norfluoxetine, or a pharmaceutically acceptable salt, solvate, hydrate, or clathrate thereof. Preferred pharmaceutical compositions and pharmaceutical unit dosage forms comprise an enantiomerically pure enantiomer of norfluoxetine (e.g., R-norfluoxetine), or a pharmaceutically acceptable salt, solvate, hydrate, or clathrate thereof.

3.1. BRIEF DESCRIPTION OF THE DRAWINGS

The unexpected activity of racemic norfluoxetine can be understood with reference to the figures described below:

FIG. 1 shows the inhibition of PGE$_2$ secretion in cultures of the human lung fibroblast cell line WI-38 to which 10 μM of various compounds have been added, wherein "Dex" is dexamethasone, "Indo" is indomethacin, "NS398" and "celebrex" are specific inhibitors of prostaglandin synthetase 2, "RS" is racemic fluoxetine, "R" is R-fluoxetine, "S" is S-fluoxetine, "nor" is racemic norfluoxetine, and "ami" is amitriptylene.

Figure 2:
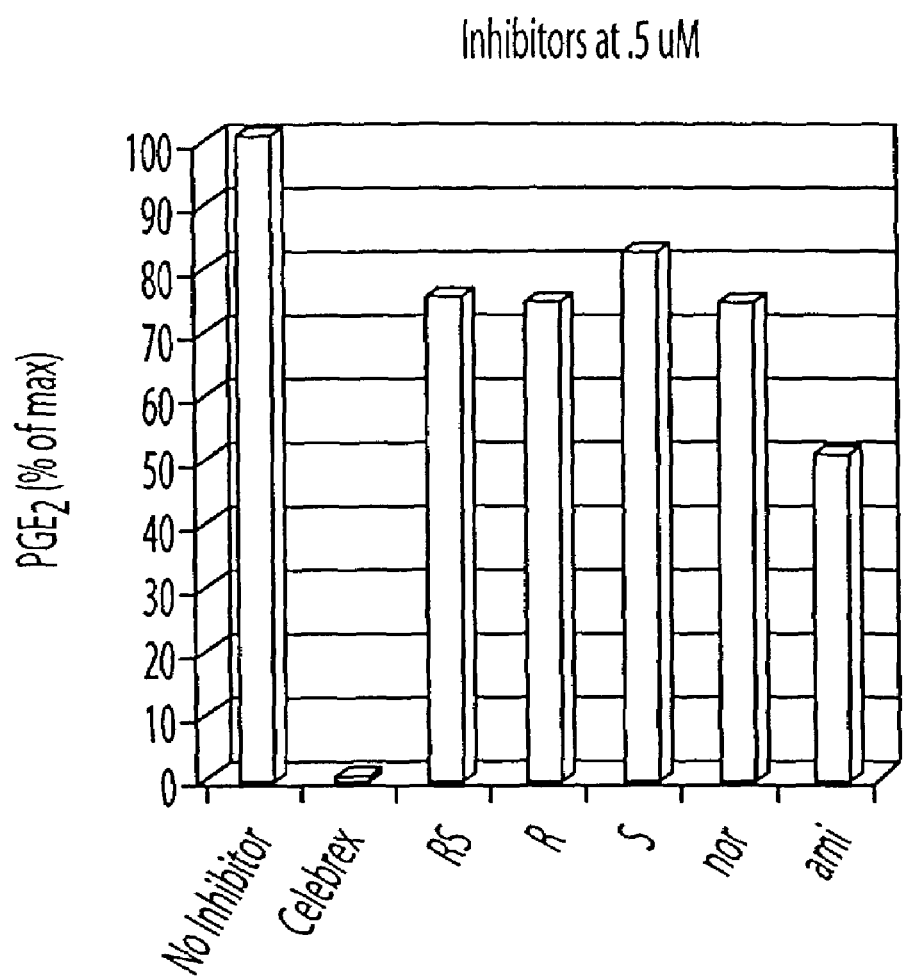

FIG. 2 shows the inhibition of $PGE_2$ secretion in cultures of the human lung fibroblast cell line WI-38 to which 0.5 μM of various compounds have been added, wherein "Dex" is dexamethasone, "Indo" is indomethacin, "NS398" and "celebrex" are specific inhibitors of prostaglandin synthetase 2, "RS" is racemic fluoxetine, "R" is R-fluoxetine, "S is S-fluoxetine, "nor" is racemic norfluoxetine, and "ami" is amitriptylene.

3.2. DEFINITIONS

As used herein, the term "prodrug" means a derivative of a compound that can hydrolyze, oxidize, or otherwise react under biological conditions (in vitro or in vivo) to provide the compound. Examples of prodrugs include, but are not limited to, derivatives of topoisomerase inhibitors or thalidomide that comprise biohydrolyzable moieties such as biohydrolyzable amides, biohydrolyzable esters, biohydrolyzable carbamates, biohydrolyzable carbonates, and biohydrolyzable ureides.

As used herein, the terms "biohydrolyzable carbamate," "biohydrolyzable carbonate," and "biohydrolyzable ureide" mean a carbamate, carbonate, or ureide, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein, the term "biohydrolyzable ester" means an ester of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, alkoxyacyloxy esters, alkyl acylamino alkyl esters, and choline esters.

As used herein, the term "biohydrolyzable amide" means an amide of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable amides include, but are not limited to, lower alkyl amides, α-amino acid amides, alkoxyacyl amides, and alkylaminoalkylcarbonyl amides.

As used herein, the term "pharmaceutically acceptable salt" refers to a salt prepared from a pharmaceutically acceptable non-toxic inorganic or organic acid. Suitable non-toxic acids include, but are not limited to, acetic, benzenesulfonic, benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, and p-toluenesulfonic acids. For example, specific pharmaceutically acceptable salts are hydrochloride and maleic acid salts.

As used herein, the terms "enantiomerically pure," "pure enantiomer," and "enantiomerically pure enantiomer" mean a composition that comprises one enantiomer of a compound and is substantially free of the opposite enantiomer of the compound. A typical enantiomerically pure compound comprises greater than about 80% by weight of one enantiomer of the compound and less than about 20% by weight of the opposite enantiomer of the compound, more preferably greater than about 90% by weight of one enantiomer of the compound and less than about 10% by weight of the opposite enantiomer of the compound, even more preferably greater than about 95% by weight of one enantiomer of the compound and less than about 5% by weight of the opposite enantiomer of the compound, and most preferably greater than about 99% by weight of one enantiomer of the compound and less than about 1% by weight of the opposite enantiomer of the compound. For example, enantiomerically pure R-norfluoxetine comprises at least about 80% by weight R-norfluoxetine and less than about 20% by weight S-norfluoxetine.

As used herein, a composition that is "substantially free" of a compound means that the composition contains less than about 20% by weight, more preferably less than about 10% by weight, even more preferably less than about 5% by weight, and most preferably less than about 1% by weight of the compound. For example, the phrase "R-norfluoxetine substantially free of S-norfluoxetine" is accorded the same meaning as "enantiomerically pure R-norfluoxetine."

4. DETAILED DESCRIPTION OF THE INVENTION

This invention is based, in part, on the discovery that specific metabolites of certain serotonin reuptake inhibitors, and enantiomerically pure isomers thereof, exhibit anti-inflammatory activity.

A first embodiment of the invention encompasses a method of inhibiting or reducing the production of $PGE_2$, which comprises contacting a cell that produces $PGE_2$ with an amount of norfluoxetine, or a pharmaceutically acceptable salt, solvate, hydrate, or clathrate thereof, sufficient to inhibit or reduce the production of $PGE_2$. Preferably, the norfluoxetine is enantiomerically pure R- or S-norfluoxetine. More preferably, the norfluoxetine is enantiomerically pure R-norfluoxetine.

A second embodiment of the invention encompasses a method of treating or preventing inflammation in a patient (e.g., a mammal, preferably a human) which comprises administering to a patient in need of such treatment or prevention a therapeutically or prophylactically effective amount of norfluoxetine, or a pharmaceutically acceptable salt, solvate, hydrate, or clathrate thereof. Preferably, the norfluoxetine is enantiomerically pure R- or S-norfluoxetine. More preferably, the norfluoxetine is enantiomerically pure R-norfluoxetine.

A third embodiment of the invention encompasses a method of treating or preventing a disease or disorder selected from the group consisting of autoimmune diseases (e.g., lupus erythematosus and multiple sclerosis), arthritis (e.g., rheumatoid arthritis and osteoarthritis), neurologic diseases (e.g., Alzheimer's dementia, amyotrophic lateral sclerosis and Parkinson's disease), inflammatory diseases (e.g., sepsis, adult respiratory distress syndrome, inflammatory bowel disease, and diseminated intravascular coagulation), fibromyalgia, pain resulting from inflammation (e.g., hyperalgesia and allodynia), neuropathic pain, and cancer (e.g., colon cancer and rectal cancer), which comprises administering to a patient in need of such treatment or prevention a therapeutically or prophylactically effective amount of norfluoxetine, or a pharmaceutically acceptable salt, solvate, hydrate, or clathrate thereof. Preferably, the norfluoxetine is enantiomerically pure R- or S-norfluoxetine. More preferably, the norfluoxetine is enantiomerically pure R-norfluoxetine.

In each method of treating or preventing a disease or disorder, the racemic or enantiomerically pure norfluoxetine, or pharmaceutically acceptable salt, solvate, hydrate, or clathrate thereof, can be administered in combination with a second active ingredient. Examples of second active ingredients include, but are not limited to, anti-inflammatory drugs, analgesics, proton-pump inhibitors, and uricosuric agents. Examples of anti-inflammatory drugs include, but are not limited to, corticosteroids, NSAIDs, leukotriene inhibitors, gold complexes, and antihistamines.

A fourth embodiment of the invention encompasses a pharmaceutical composition adapted for the treatment or prevention of inflammation which comprises norfluoxetine, or a pharmaceutically acceptable salt, solvate, hydrate, or clathrate thereof in an amount sufficient to alleviate or prevent inflammation in a patient. A typical pharmaceutical composition further comprises a pharmaceutically acceptable excipient or diluent. Preferably, the norfluoxetine is enantiomerically pure R- or S-norfluoxetine. More preferably, the norfluoxetine is enantiomerically pure R-norfluoxetine.

A fifth embodiment of the invention encompasses a pharmaceutical unit dosage form adapted for the treatment or prevention of inflammation which comprises norfluoxetine, or a pharmaceutically acceptable salt, solvate, hydrate, or clathrate thereof in an amount sufficient to alleviate or prevent inflammation in a patient. A typical pharmaceutical composition further comprises a pharmaceutically acceptable excipient or diluent. Preferably, the norfluoxetine is enantiomerically pure R- or S-norfluoxetine. More preferably, the norfluoxetine is enantiomerically pure R-norfluoxetine.

Preferred pharmaceutical compositions and unit dosage forms of the invention comprise a pharmaceutically acceptable excipient or diluent. Specific pharmaceutical compositions and unit dosage forms further comprise a second active ingredient. Examples of second active ingredients include, but are not limited to, anti-inflammatory drugs, analgesics, proton-pump inhibitors, and uricosuric agents. Examples of anti-inflammatory drugs include, but are not limited to, corticosteroids, NSAIDs, leukotriene inhibitors, gold complexes, and antihistamines.

Pharmaceutical unit dosage forms of this invention are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient.

A sixth embodiment of the invention encompasses a kit for use in the treatment or prevention of a disease or disorder which comprises a therapeutically effective amount of norfluoxetine, or a pharmaceutically acceptable salt, solvate, hydrate, or clathrate thereof, and a therapeutically effective amount of a second active ingredient. Preferably, the norfluoxetine is enantiomerically pure R- or S-norfluoxetine. More preferably, the norfluoxetine is enantiomerically pure R-norfluoxetine. Examples of second active ingredients include, but are not limited to, anti-inflammatory drugs, analgesics, proton-pump inhibitors, and uricosuric agents. Examples of anti-inflammatory drugs include, but are not limited to, corticosteroids, NSAIDs, leukotriene inhibitors, gold complexes, and antihistamines.

A seventh embodiment of the invention encompasses a method of preparing an enantiomerically pure enantiomer of norfluoxetine which comprises asymmetrically reducing an alkyl ester of 3-benzoylpropionic acid, preferably using borane in the presence of a chiral catalyst such as, but not limited to, (S)- or (R)-Me CBS or (+)- or with (−)-chlorodiisopinocamphenylborane (DIPCl®); reacting either the resulting hydroxy ester or lactone with a base in alcohol, preferably, ammonium hydroxide in methanol to (R)- or (S)-4-hydroxy-4-phenyl butyramide; treating with an oxidant such as, but not limited to, iodobenzene diacetate, alkaline bromine, lead tetraacetate, ammonium tribromide complexes, alkaline solution of N-bromosuccinamide to provide a cyclic carbamate; reacting the cyclic carbamate with a base, such as potassium hydroxide or sodium hydroxide in a solvent such as, but not limited to, water or isopropanol; and treating with a base and 4-chloro-trifluoromethylbenzene to afford enantiomerically pure (R)- or (S)-norfluoxetine.

An eighth embodiment of the invention encompasses novel salts of enantiomerically pure enantiomers of norfluoxetine and their preparations. One such salt is (R)-norfluoxetine.(D)-tartarate. Another is (S)-norfluoxetine.(L)-tartarate. The enantiomerically pure salts of norfluoxetine can be prepared by contacting (R)- or (S)-norfluoxetine, with a salt such as, but not limited to, (L)- or (D)-tartaric acid and a solvent, preferably methanol.

4.1. Preparation of Norfluoxetine and its Enantiomers and Determination of their Biological Activity Norfluoxetine can be readily prepared using techniques known to those skilled in the art. For example, it can be prepared by demethylating fluoxetine, which in turn can be prepared by methods such as those disclosed in U.S. Pat. No. 5,648,396, which is incorporated herein by reference. Demethylation can be achieved using any number of conventional methods. See, e.g., J. March, *Advanced Organic Chemistry* 407–408 ($4^{th}$ ed.; 1992).

Enantiomerically pure enantiomers of norfluoxetine can be isolated by techniques known in the art. Examples include, but are not limited to, the formation of chiral salts and the use of chiral or high performance liquid chromatography (HPLC) and the formation and crystallization of chiral salts. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, N.Y., 1962); and Wilen, S. H., *Tables of Resolving Agents and Optical Resolutions* p. 268 (E. L. Eliel, Ed., Univ. of Notre Dame Press, Notre Dame, Ind., 1972).

A preferred method of preparing enantiomerically pure enantiomers of norfluoxetine comprises the asymmetric synthesis of the compound from 3-benzoylpropionic acid. According to this method, 3-benzoylpropionic acid is methylated to provide methyl 3-benzylpropionate, which is then contacted with (+)-B-chlorodiisopinocamphenylborane chloride ((+)-DIP-Cl) to provide (R)-χ-phenyl-χ-butrolactone if R-norfluoxetine is being prepared, or with (−)-DIP-Cl to provide (S)-χ-phenyl-χ-butrolactone if S-norfluoxetine is being prepared. The lactone is subsequently contacted with ammonia to provide the corresponding chiral 4-hydroxy-4-phenylbutanamide (i.e., (R)- or (S)-4-hydroxy-4-phenylbutanamide). A cyclic carbamate is then prepared from the amide by contacting the chiral 4-hydroxy-4-phenylbutanamide with iodobenzene diacetate. The carbamate is then contacted with base to provide chiral 3-amino-(1R)-phenylpropanol-1-ol, which is subsequently converted to the corresponding enantiomer of norfluoxetine free base by contacting it with sodium hydride and 4-chlorobenzotrifluoride. This free base can then be converted into a salt by known methods. For example, (D)-tartaric acid can be contacted with (R)-norfluoxetine free base to provide (R)-norfluoxetine.(D)-tartarate. Similarly, (L)-tartaric acid can be contacted with (S)-norfluoxetine free base to provide (S)-norfluoxetine.(L)-tartarate.

An example of this method is shown below in Scheme I:

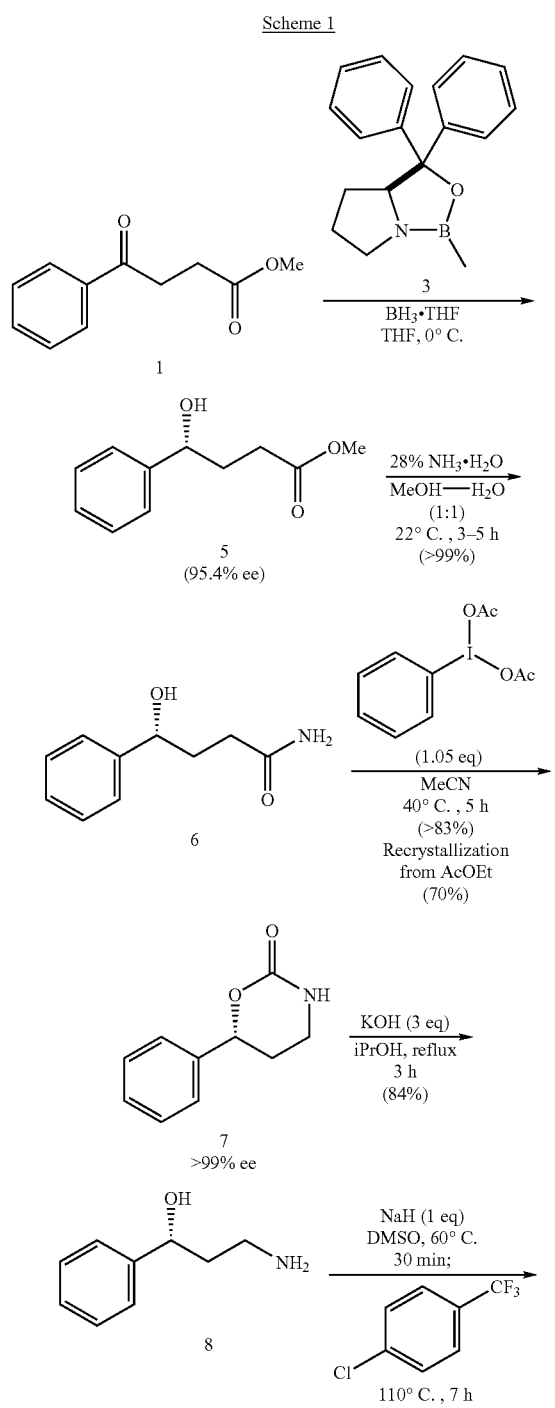

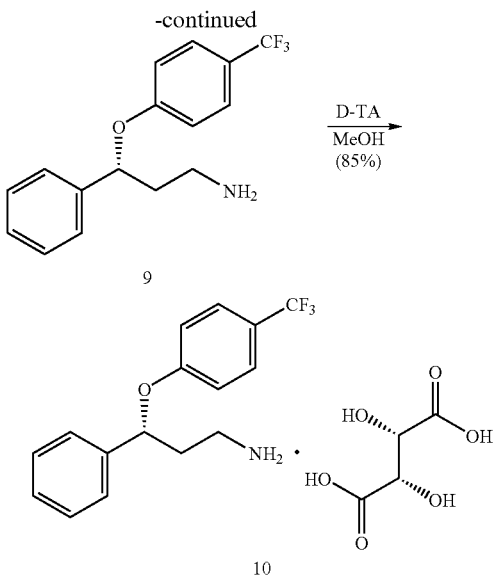

The biological activity of norfluoxetine and enantiomerically pure enantiomers of norfluoxetine can be determined using in vitro and in vivo assays known to those skilled in the art. Examples of in vitro assays include, but are not limited to, the use of WI-38 cells. See, e.g., Lin et al, *JBC* 267:23451–23454 (1992); Patil et al., *Blood* 85:80–86 (1995). In vitro assays using IMR-90 cells have also been reported. See, e.g., Endo et al., *Am. J. Respir. Cell. Md. Biol.* 12:358–365 (1995). Further examples are provided herein.

4.2. Methods of Treatment and Prevention

This invention encompasses methods of treating and preventing disease and disorders which include, but are not limited to, inflammation, autoimmune diseases (e.g., lupus erythematosus and multiple sclerosis), arthritis (e.g., rheumatoid arthritis and osteoarthritis), neurologic diseases (e.g., Alzheimer's dementia, amyotrophic lateral sclerosis and Parkinson's disease), inflammatory diseases (e.g., sepsis, adult respiratory distress syndrome, inflammatory bowel disease, and diseminated intravascular coagulation), fibromyalgia, pain resulting from inflammation (e.g., hyperalgesia and allodynia), neuropathic pain, and cancer (e.g., colon cancer and rectal cancer) in mammals, and in humans in particular.

Methods of the invention may, for example, be used to treat or prevent chronic and/or acute diseases and conditions. Methods disclosed herein may also be used to treat or prevent local and/or systemic conditions. For example, they may be used to treat or prevent inflammation of a wide variety of tissues and organs such as, but are not limited to, the skin, muscles, connective tissue (e.g., tendons and ligaments), blood vessels, nervous tissue, joints, the gastrointestinal tract (e.g., the stomach and the large and small intestine), the liver, the spleen, the lungs, and the kidneys.

Methods of the invention comprise the administration of a therapeutically or prophylactically effective amount of a first active ingredient (e.g., enantiomerically pure R-norfluoxetine, or a pharmaceutically acceptable salt, solvate, hydrate, or clathrate thereof), optionally in combination with a second active ingredient. Optional second active ingredients can be administered to a patient before, concurrently with, or after the administration of the first active ingredient by the same or by a different route of administration.

Optional second active ingredients include, but are not limited to, anti-inflammatory drugs, analgesics, proton-pump inhibitors, and uricosuric agents. Examples of anti-inflammatory drugs include, but are not limited to, corticosteroids, NSAIDs, leukotriene inhibitors, gold complexes, and antihistamines.

Examples of corticosteroids include, but are not limited to, alclometasone, amcinonide, beclomethasone, betamethasone, clobetasol, clocortolone, cortisol, prednisolone, and pharmaceutically acceptable salts, solvates, clathrates, prodrugs, and active metabolites and stereoisomers thereof.

Examples of NSAIDS include, but are not limited to, acetominaphen, apazone, diclofenac, etodolac, fenoprofen, flurbiprofen, ibuprofen, indomethacin, ketorolac, ketoprofen, meclofenamate, mefenamic acid, meloxicam, nabumetone, naproxen, nimesulide, oxaprozin, oxyphenthatrazone, phenylbutazone, piroxicam, salicylates, sulindac, tenoxicam, tolmetin, and pharmaceutically acceptable salts, solvates, clathrates, prodrugs, and active metabolites and stereoisomers thereof. Examples of salicylates include, but are not limited to, aspirin, sodium salicylate, choline magnesium trisalicylate, salsalate, diflunisal, salicylsalicylic acid, sulfasalazine, and olsalazine.

Examples of leukotriene inhibitors include, but are not limited to, docebenone, ICI-D2318, MK-0591, MK-886, piripost, zileuton, and pharmaceutically acceptable salts, solvates, clathrates, prodrugs, and active metabolites and stereoisomers thereof.

Examples of antihistamines include, but are not limited to, acrivastine, astemizole, brompheniramine, carbinoxamine, cetirazine, chlorcyclizine, chlorpheniramine, clemastine, cyclizine, descarboxyloratadine, dimenhydrinate, diphenhydramine, hydroxyzine, levocabastine, loratadine, promethazine, pyrilamine, terfenadine, tripelennamine, and pharmaceutically acceptable salts, solvates, clathrates, prodrugs, and active metabolites and stereoisomers thereof.

Examples of analgesics include, but are not limited to, bremazocine, buprenorphine, butorphanol, codeine, CTOP, [D-Ala$^2$,Glu$^4$]deltorphin, DAMGO, diprenorphine, DPDPE, DSLET, dynorphin A, dynorphin B, β-endorphin, ethylketocyclazocine, etorphine, fentanyl, β-funaltrexamine, heroin, hydrocodone, hydromorphone, leu-enkephalin, levophanol, levallorphan, meptazinol, met-enkephalin, methadone, morphine, oxycodone, oxymorphone, nalbuphine, nalmefene, nalorphine, naloxonazine, naloxone, naloxone benzoylhydrazone, naltrexone, naltrindole, α-neoendorphin, nor-binaltorphimine, pentazocine, propoxyphene, spiradoline, 50,488, U69,593, and pharmaceutically acceptable salts, solvates, clathrates, prodrugs, and active metabolites and stereoisomers thereof.

Examples of proton-pump inhibitors include, but are not limited to, prazole derivatives, such as omeprazole, lansoprazole, pantoprazole, rabeprazole, and pharmaceutically acceptable salts, solvates, clathrates, prodrugs,and active metabolites and stereoisomers thereof. Active metabolites of proton-pump inhibitors can also be employed as an optional second active ingredient. Examples of such metabolites include, but are not limited to, hydroxy-omeprazole, hydroxy-lansoprazole, the carboxylic acid derivative of omeprazole, and desmethyl-pantoprazole.

Examples of uricosuric agents include, but are not limited to, allopurinol, benzbromarone, colchicine, probenecid, sulfinpyrazone, and pharmaceutically acceptable salts, solvate, hydrates, clathrates, and active metabolites and stereoisomers thereof.

The magnitude of a prophylactic or therapeutic dose of each active ingredient in the acute or chronic management of a disease or disorder will vary with the disorder itself, the specific active ingredients, and the route of administration. The dose and/or dose frequency may also vary according to age, body weight, response, and the past medical history of the patient. Suitable dosing regimens can be readily selected by those skilled in the art with due consideration of such factors by following, for example, dosages reported in the literature and recommended in the *Physician's Desk Reference*® (54$^{th}$ ed., 2000).

Unless otherwise indicated, the magnitude of a prophylactic or therapeutic dose of each active ingredient used in an embodiment of the invention will be that which is safe and effective (e.g., has received regulatory approval).

In one embodiment of the invention, a first active ingredient (e.g., enantiomerically pure R- or S-norfluoxetine) is administered orally as needed in an amount of from about 1 mg to about 500 mg, preferably in an amount of from about 10 mg to about 300 mg, more preferably in an amount of from about 15 mg to about 200 mg, and most preferably in an amount of from about 20 mg to about 100 mg. The dosage amounts and frequencies provided above are encompassed by the terms "therapeutically effective," "prophylactically effective," and "therapeutically or prophylactically effective" as used herein.

The suitability of a particular route of administration employed for a particular active ingredient will depend on the active ingredient itself (e.g., whether it can be administered orally without decomposing prior to entering the blood stream) and the disease or disorder to be treated or prevented. For example, topical administration is typically preferred for treating or preventing local inflammation of the skin, while oral or parenteral administration is typically preferred for systemic inflammation or inflammation within the body. Similarly, oral or parenteral administration may be preferred for the treatment or prevention of acute inflammation, whereas transdermal or subcutaneous routes of administration may be employed for treatment or prevention of a chronic disease or disorder.

The optional administration of a second active ingredient will also depend on the disease or disorder to be treated or prevented. For example, uricosuric agents are preferably used in the treatment or prevention of inflammation of the bowel (e.g., gerd), while gold complexes are preferably used in the treatment or prevention of inflammation of the joints (e.g., rheumatoid arthritis).

4.3. Pharmaceutical Compositions and Dosage Forms

Pharmaceutical compositions and dosage forms of the invention comprise one or more of the active ingredients disclosed herein (e.g., enantiomerically pure R- or S-norfluoxetine, or a pharmaceutically acceptable prodrug, salt, solvate, hydrate, or clathrate thereof). Pharmaceutical compositions and dosage forms of the invention typically also comprise one or more pharmaceutically acceptable excipients or diluents.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of inflammation or a related disorder may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., *Remington's Pharmaceutical Sciences,* 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients, and norfluoxetine and its enantiomerically pure enantiomers in particular, can be accelerated by some excipients such as lactose, or when exposed to water. Active ingredients that comprise primary or secondary amines (e.g., norfluoxetine and its enantiomerically pure enantiomers) are particularly susceptible to such accelerated decomposition. Consequently, this invention encompasses pharmaceutical compositions and dosage forms that contain little, if any, lactose other mono- or di-saccharides. As used herein, the term "lactose-free" means that the amount of lactose present, if any, is insufficient to substantially increase the degradation rate of an active ingredient.

Lactose-free compositions of the invention can comprise excipients that are well known in the art and are listed, for example, in the U.S. Pharmocopia (USP) SP (XXI)/NF (XVI). In general, lactose-free compositions comprise active ingredients, a binder/filler, and a lubricant in pharmaceutically compatible and pharmaceutically acceptable amounts. Preferred lactose-free dosage forms comprise active ingredients, microcrystalline cellulose, pre-gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379–80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise racemic or enantiomerically pure norfluoxetine, or a pharmaceutically acceptable salt, solvate, clathrate, hydrate, or prodrug thereof in an amount of from about 1 mg to about 500 mg, preferably in an amount of from about 10 mg to about 300 mg, more preferably in an amount of from about 15 mg to about 200 mg, and most preferably in an amount of from about 20 mg to about 100 mg.

4.3.1. Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 18th ed., Mack Publishing, Easton Pa. (1990).

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, PA), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

An example of a preferred liquid oral dosage form of the invention comprises 20 mg/5 mL R-norfluoxetine hydrochloride in a solution containing alcohol 0.23%, benzoic acid, flavoring agent, glycerin, purified water, and sucrose. A preferred caplet dosage form of the invention comprises 20 mg R-norfluoxetine hydrochloride, gelatin, iron oxide, silicone, starch, and titanium dioxide.

4.3.2. Delayed Release Dosage Forms

Active ingredients of the invention can be administered by controlled release means or by delivery devices that are well known to those of ordinary skill in the art. Examples include, but are not limited to, those described in U.S. Pat. Nos.: 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

4.3.3. Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

4.3.4. Transdermal, Topical, and Mucosal Dosage Forms

Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., *Remington's Pharmaceutical Sciences*, 16th and 18th eds., Mack Publishing, Easton Pa. (1980 & 1990); and *Introduction to Pharmaceutical Dosage Forms*, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied.

With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., *Remington's Pharmaceutical Sciences*, 16th and 18th eds., Mack Publishing, Easton Pa. (1980 & 1990).

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

4.3.5. Kits

Typically, active ingredients of the invention are preferably not administered to a patient at the same time or by the same route of administration. This invention therefore encompasses kits which, when used by the medical practitioner, can simplify the administration of appropriate amounts of active ingredients to a patient.

A typical kit of the invention comprises a unit dosage form of racemic or enantiomerically pure norfluoxetine, or a pharmaceutically acceptable prodrug, salt, solvate, hydrate, or clathrate thereof, and a unit dosage form of a second active ingredient. Examples of second active ingredients include, but are not limited to, anti-inflammatory drugs, analgesics, and proton-pump inhibitors. Examples of second anti-inflammatory drugs include, but are not limited to, corticosteroids, NSAIDs, gold complexes, and antihistamines.

Kits of the invention can further comprise devices that are used to administer the active ingredients. Examples of such devices include, but are not limited to, syringes, drip bags, patches, and inhalers.

Kits of the invention can further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

5. EXAMPLES

Certain embodiments of the invention, as well as certain novel and unexpected advantages of the invention, are illustrated by the following non-limiting examples.

5.1. Example 1

Synthesis of R-Norfluoxetine.(D)-Tartarate

The 3-benzoylpropionic acid starting material is available from Aldrich, Acros and Lancaster. The methyl ester (Methyl 3-benzoylpropionate) is also available from Lancaster.

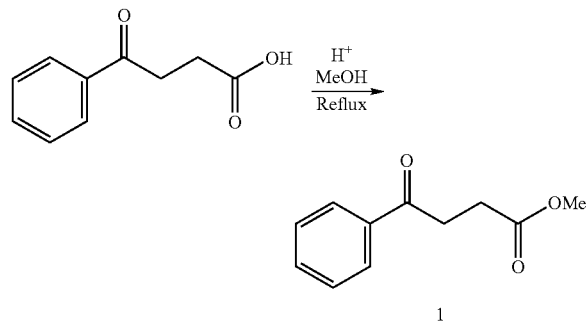

Methyl 3-Benzoylpropionate (1): To a 1.0 L round bottom flask was added 89 g (0.5 mol) of 3-benzoylpropionic acid and 200 mL of methanol. The solution was stirred until all of the acid had dissolved. To this solution was added approximately 2.0 mL of conc. $H_2SO_4$ and the reaction refluxed for 2.5 hours. After the reaction was determined to be complete, the methanol was removed on the rotoevaporator and to the residual oil was added ethyl acetate (~500 mL). To the ethyl acetate layer was then added 150 mL of a saturated sodium carbonate solution. The layers were extracted and allowed to separate. The organic layer was then dried ($MgSO_4$), filtered, and concentrated to yield methyl 3-benzoylpropionate (1) as a light yellow oil. Yield 96 g; yield 100%; >97% cp. Lit bp 172–174° C. at 10 mm Hg.; $^1$H NMR ppm (δ), $CDCl_3$ 7.98 (dd, 2H), 7.54 (m, 1H), 7.45 (m, 2H), 3.70 (s, 3H, $OCH_3$), 3.32 (t, 2H), 2.76 (t, 2H). $^{13}$C NMR ppm (δ), $CDCl_3$ 198.0 (C=O), 173.3 ($CO_2$), 136.5 (q), 133.2, 128.6, 128.0, 51.7 ($OCH_3$), 33.3, 28.0. IR oil cm$^{-1}$ 2952, 1737, 1687, 1596, 1449, 1358, 1221, 1168 1001, 750, 691.

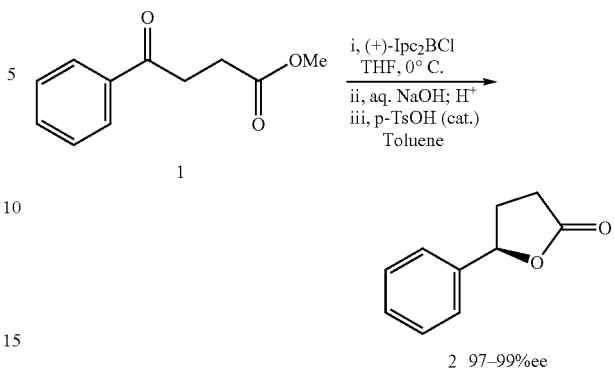

Preparation of (R)-γ-phenyl-γ-butrolactone (2): To a 500 mL round bottom flask was added 30.5 g (0.0951 mol) of (+)-DIP-Cl[(-)-B-chlorodiisopinocamphenylborane]. To this was added 30 mL of dry THF at room temperature over 15 minutes. Once dissolved, the solution was cooled to 0° C. While maintaining the temperature 0° C., to this solution was added dropwise 10.80 g (0.0561 mol) of methyl 3-benzoylpropionate (1) in 15 mL of dry THF over 30 minutes.

During the addition of the ketoester, the reaction mixture turned milky white in color and after all of the material was added the reaction mixture turned clear. The reaction was maintained between 0° C. for 8 hours, and the reaction progress was monitored by HPLC using the method outlined previously. After 8 hours, the reaction mixture was allowed to warm to 22° C. The reaction was stopped after all of the starting material was gone. [typical retention time: Ketoester (IIa)=6.9 minutes; Alcoholester (III)=4.9 min]. To the reaction mixture was then added slowly 26 mL of water (1.44 mol) over 10 minutes keeping the temperature below 10° C. Methanol was then added (66 mL, 1.63 mol) followed by 76 mL of a 5 M aqueous NaOH solution keeping the temperature below 10° C. The mixture was stirred for 2 hours and checked periodically by HPLC. After 2 hours the reaction was shown to be complete [Retention Time Alcohol Acid (IV)=3.4 min]. The light yellow solution was poured into 500 mL of MTBE and 200 mL of saturated $NaHCO_3$ solution. After the extraction the layers were separated and the aqueous layer re-extracted with 200 mL of MTBE. The layers were again separated and the aqueous layer acidified to pH=2 with concentrated HCl. The aqueous layer was saturated with NaCl and then extracted 3 times with 300 mL of ethyl acetate. The ethyl acetate layer was rotoevaporated and the residue taken up in toluene (1000 mL). To the toluene was added 1.5 g (0.006 mol) of PPTS and heated to reflux for 2 hours until the lactonization was complete. The solution was cooled to room temperature and washed twice with an saturated aq. $NaHCO_3$ solution. The toluene layer was rotoevaporated to yield 8.36 g (92%) of the lactone (2). The chemical purity is 97.3%, and the optical purity is 98.75 ip (shown below). Achiral HPLC Retention Time=5.8 min. Chiral Retention Time=26.0 min. (R), 30.1 min. (S). $^1$H NMR ppm (δ), $CDCl_3$ 7.34–7.25 (m, 5H), 5.47 (t, 1H), 2.68–2.60 (m, 3H), 2.22–2.10 (m, 1H). $^{13}$C NMR ppm (δ), $CDCl_3$ 176.9 (C=O), 139.3(q), 128.6, 128.3, 125.2, 81.1 (C—O), 30.8, 28.8.

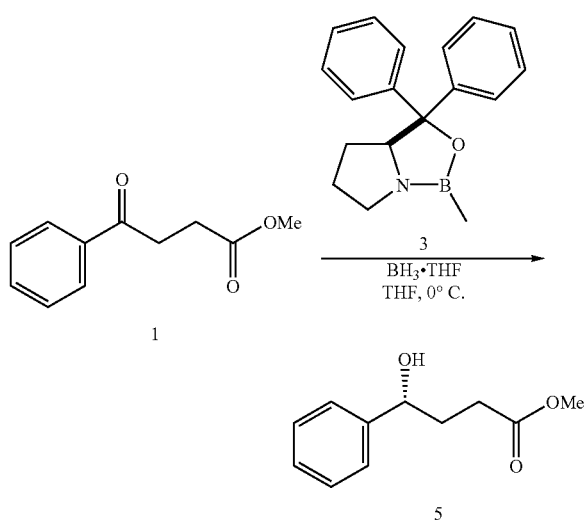

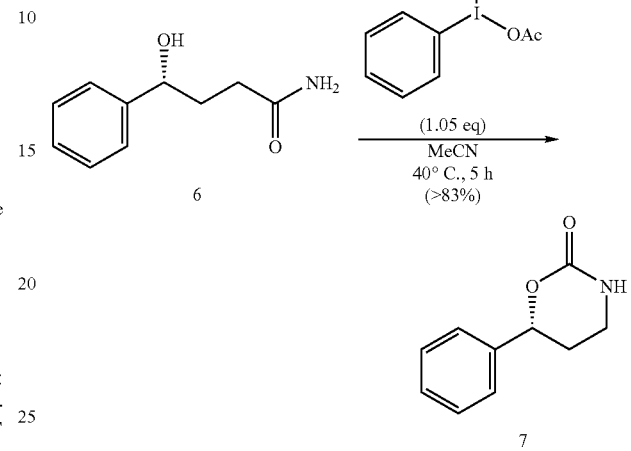

mp=74–75° C. $^1$H NMR ppm (δ), CDCl$_3$ 7.35–7.24 (m, 5H), 5.79 (s, 2H, NH$_2$), 4.77 (dd, 1H, CH—O), 3.66 (s, 1H, OH), 2.40–2.21 (m, 2H), 2.11–2.00 (m, 2H). $^{13}$C NMR ppm (δ), CDCl$_3$ 176.4 (C=O), 144.6(q), 128.7, 127.7, 126.0, 73.7 (C—O), 34.3, 32.3.

Preparation of methyl (R)-4-hydroxy-4-phenylbutyrate (5): To a dry 250 mL round bottom flask were added (S)-Me-CBS (5 mL, 1.0 M in toluene, 5.0 mmol) and 50 mL of THF under argon. The solution was cooled to −5° C. To this solution were added simultaneously BH$_3$.THF (50 mL, 1.0 M in THF, 50 mmol) and ketoester 1 in neat (9.6 g, 50 mmol) via syringe. The addition was completed in 30 min. The reaction mixture was stirred at the same temperature for another 30 minutes and worked up by addition of aqueous K$_2$CO$_3$ solution. After stirring for 30 minutes, the organic layer was separated, and the aqueous layer was extracted with AcOEt. The combined organic layers were washed with brine and dried over (Na$_2$SO$_4$). Revomal of solvent gave a pale yellow oil, containing the hydroester 5 and the CBS catalyst (ca. 11 g). The crude product could be used directly for next reaction. A sample was purified by hydrolysis with 3 N NaOH, and converted into lactone 2 by azeotropically reflux with toluene. E.e was measured by HPLC on lactone 2 (95.6%)

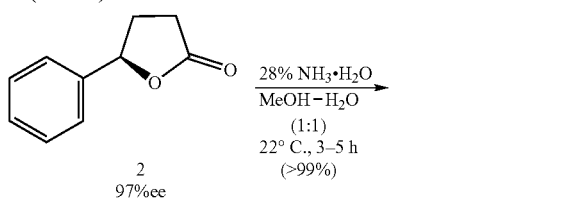

Preparation of (R)-4-hydroxy-4-phenylbutanamide (6): To a 100 mL round bottom flask was added 9 g (55.56 mmol) of the chiral lactone (2). To this oil was added 30 mL of methanol and 28–30% aqueous ammonia (30 mL, 257 mmol). This solution was stirred at room temperature for 6 hours which at this point the reaction completed. The ammonia in methanol was removed on the rotoevaporator and to the residual oil was added approximately 20 mL of ethyl acetate. The ethyl acetate was allowed to evaporate slowly and yielded a white solid (11.12 g, 100%), Preparation of the Cyclic Carbamate (7): To a 250 mL round bottom flask was added 11 g (62.12 mmol) of the chiral alcohol amide (6). The material was dissolved in 150 mL of acetonitrile and then added with 20.8 g (64.60 mmol) of iodobenzene diacetate. The solution was stirred at 40° C. for 5 hours monitoring the reaction by HPLC. After the reaction was complete, the acetonitrile was removed on the rotoevaporator. The crude pale yellow solide (9.1 g, 83%) was recrystallized from ethyl acetate to give 5.5 g of the pure product (51% yield). Chemical purity=100%, Isomeric Purity=99.7%, mp=191–192° C. Achiral HPLC Retention Time=3.6 min. Chiral Retention Time=18.1 min. (R), 22.7 min. (S). $^1$H NMR ppm (δ), CDCl$_3$ 7.37–7.29 (m, 5H), 6.65 (s, 1H, NH), 5.34 (dd, 1H, CH—O), 3.48–3.36 (m, 2H), 2.19–2.05 (m, 2H). $^{13}$C NMR ppm (δ), CDCl$_3$ 155.3 (C=O), 139.3 (q), 128.8, 128.6, 125.9, 78.8 (C—O), 39.0, 28.9. IR KBr cm$^{-1}$ 3303, 1690, 1664, 1482, 1457, 1300, 1137, 1051, 767, 756, 697.

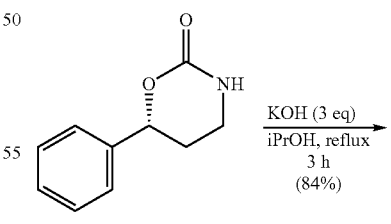

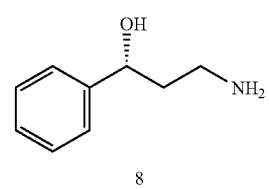

Preparation of 3-amino-(1R)-phenyl-propan-1-ol (8): To a 1 L round bottom flask was added 66 g (372.88 mmol) of the cyclic carbamate (7). To this was added 200 mL of isopropanol, 200 mL of H$_2$O followed by 45 g of KOH (803.57 mmol, 2.2 equiv). This solution was refluxed for 3 hours and then allowed to cool to room temperature. The IPA layer was separated and the aqueous layer was extracted with IPA once more (50 mL). The combined organic layers were washed with brine (1×15 mL), and concentrated on the rotoevaporator to obtain an oil. The oil was dried by azeotropically reflux with toluene and used for next reaction. 47 g of 8 was obtained as pale yellow oil (84%). $^1$H NMR ppm ($\delta$), CDCl$_3$ 7.58–7.20 (m, 5H), 4.95 (dd, 1H), 3.10 (m, 1H), 2.98 (m, 1H), 1.94–1.70 (m, 2H). $^{13}$C NMR ppm ($\delta$), CDCl$_3$ 145.35, 128.53, 127.28, 125.91, 75.67, 40.79, 40.09.

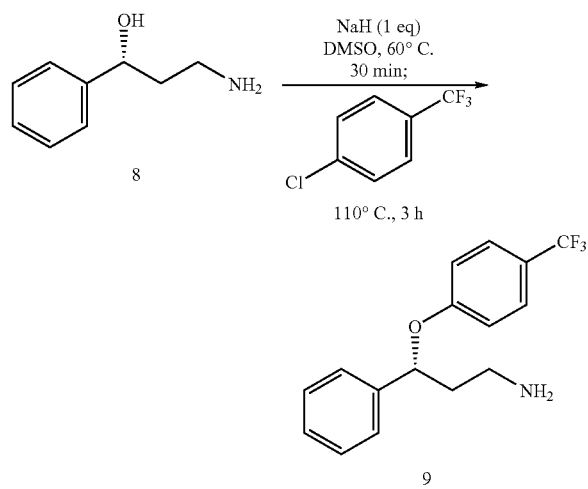

Preparation of Norfluoxetine Free Base (9): To a 100 mL round bottom flask was added 4 g (26.88 mmol) of the aminoalcohol (8) and this was dissolved in 80 mL of DMSO. To this solution was then added 1.5 g (37.5 mmol) of sodium hydride (60 wt % in oil, washed with hexanes) at 0° C. The solution was stirred at ambient temperature for 5 minutes, then heated to 70° C. for 30 min. To this dark orange solution was added 6.9 g of 4-chlorobenzotrifluoride (38.21 mmol). The reaction mixture was heated to 115° C. for 3 hours. The reaction was allowed to cool to room temperature and then poured into 15 mL of ice water to quench the reaction. The reaction mixture was extracted with ethyl ether (5×50 mL), followed by two extractions using toluene (2×50 mL). The organic layers were combined and washed twice with brine. The aqueous layer was separated and the organic layer dried, filtered, and rotoevaporated. This crude material was purified by column chromatography (silica gel) using 5% methanol:methylene chloride as the eluent. The yield of pure norfluoxetine free-base (9) is 4.1 g (69%). 1.1 g of the starting material was recovered. $^1$H NMR ppm ($\delta$), CDCl$_3$ 7.57 (d, 2H), 7.44–7.24 (m, 5H), 6.91 (d, 2H), 5.43 (dd, 1H), 3.15 (t, 2H), 2.39 (m, 1H), 2.28 (m, 1H). $^{13}$C NMR ppm ($\delta$), CDCl$_3$ 160.84, 141.34, 129.06, 128.09, 127.04, 127.00, 126.03, 116.02, 78.64, 42.54, 38.80.

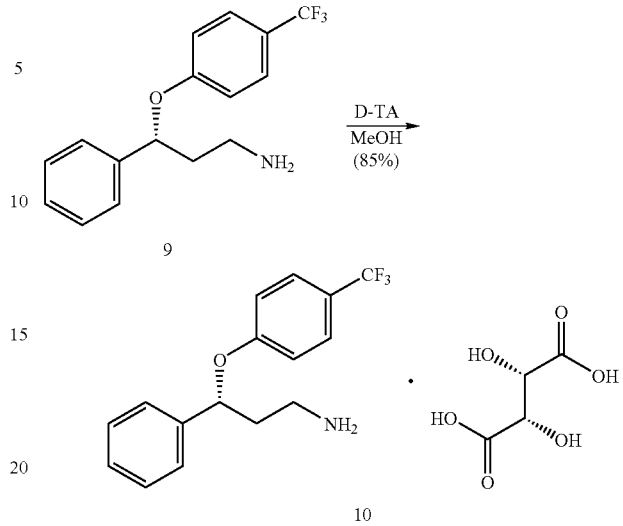

Preparation of (R)-Norfluoxetine.(D)-Tartrate (10): To a 50 mL round bottom flask was added 1.63 g (5.53 mmol) of (R)-fluoxetine free amine (9). To this was added 20 mL of methanol and the amine was dissolved. To this solution was added 840 mg of (D)-tartaric acid (5.6 mmol). The reaction mixture was stirred for 30 minutes and then methanol was rotoevaporated to dryness. The solid was slurred in 20 mL of TBME and filtered. The white solid was dried in a vacuum oven for 5 hours at ~40° C. 2.08 g of (R)-norfluoxetine (D)-tartrate was obtained (85%). 99.44% ee, 99.53 A % purity. $^1$H NMR ppm ($\delta$), DMSO 7.63–7.10 (m, 9H), 5.61 (m, 1H, CH—O), 3.90 (dd, 2H), 2.90 (m, 2H), 2.50 (s, 1H), 2.35–2.08 (m, 2H). $^{13}$C NMR ppm ($\delta$), DMSO 175.3, 160.8, 140.8, 129.5, 128.71, 127.5, 126.6, 117.0, 77.0, 72.3, 36.4.

5.2. Example 2

Inhibition of PGE$_2$ Production

Compounds were tested for anti-inflammatory activity using a whole cell-based assay, wherein the human lung fibroblast cell line WI-38 was cultured in Eagle's basal media supplemented with 10% fetal calf serum (FCS) in 48-well tissue culture dishes in a humidified 7% CO$_2$ atmosphere at 37° C. When the cells reached confluence, they were fed with fresh media for 24 hours. The media was removed and fresh media, containing either 5% or 10% FCS, was added to the cells. Compounds were added in a volume of 1 µL in either ethanol or dimethylsulfoxide (DMSO) to give the desired final concentration. Interleukin-1β (Calbiochem) in 0.1% bovine serum albumin in phosphate buffered saline was added in a 1 µL aliquot to give a final concentration of 100 pg/mL. The cells were cultured for 24 hours and the amount of PGE$_2$ secreted into the cell culture media was assayed using a PGE$_2$ enzyme immunoassay kit (Cayman Chemicals, Ann Arbor, Mich.). Inhibition of PGE$_2$ production is indicative of anti-inflammatory activity. This assay will detect either direct inhibition of the prostaglandin synthetase 2 enzyme as evidenced by the efficacy of celebrex, or it will detect the inhibition of transcription—or the activation of transcription—of the protaglandin synthetase 2 gene as evidenced by the efficacy of dexamethasone.

Using this assay, the effect of racemic or enantiomerically pure norfluoxetine in vitro is shown in FIGS. 1 and 2. Additional results are shown below in Tables 1–4.

TABLE 1

(10% fetal calf serum-containing media)

| Sample | $PGE_2$ (pg/ml) |
|---|---|
| No IL-β | low |
| +IL-β | 886 |
| celebrex 0.5 uM | low |
| celebrex 10 uM | low |
| rac-fluoxetine 0.5 uM | low |
| rac-fluoxetine 10 uM | low |
| rac-norfluoxetine 0.5 uM | 189 |
| rac-norfluoxetine 10 uM | low |
| (R)-norfluoxetine 0.5 uM | 714 |
| (R)-norfluoxetine 10 uM | 159 |
| (S)-norfluoxetine 0.5 uM | 809 |
| (S)-norfluoxetine 10 uM | 486 |
| rac-ketoprofin 10 uM | low |
| (R)-ketoprofin 0.5 uM | low |
| (R)-ketoprofin 10 uM | low |
| (S)-ketoprofin 0.5 uM | low |
| (S)-ketoprofin 10 uM | low |

TABLE 2

(5% fetal calf serum-containing media)

| Sample | $PGE_2$ (pg/ml) |
|---|---|
| No IL-1β | low |
| +IL-1β | 667 |
| celebrex 0.5 uM | 16 |
| celebrex 10 uM | low |
| rac-fluoxetine 0.5 uM | low |
| rac-fluoxetine 10 uM | low |
| rac-norfluoxetine 0.5 uM | low |
| rac-norfluoxetine 10 uM | low |
| (R)-norfluoxetine 0.5 uM | 255 |
| (R)-norfluoxetine 10 uM | 31 |
| (S)-norfluoxetine 0.5 uM | 483 |
| (S)-norfluoxetine 10 uM | 112 |
| rac-ketoprofen 0.5 uM | 119 |
| rac-ketoprofen 10 uM | low |
| (R)-ketoprofen 0.5 uM | low |
| (R)-ketoprofen 10 uM | low |
| (S)-ketoprofen 0.5 uM | 145 |
| (S)-ketoprofen 10 uM | low |

TABLE 3

(10% fetal calf serum-containing media)

| Sample | $PGE_2$ (pg/ml) |
|---|---|
| No IL-1β | low |
| +IL-1β | 1980 |
| celebrex 0.5 uM | low |
| celetrex 10 uM | low |
| rac-fluoxetine 0.5 uM | 545 |
| rac-fluoxetine 10 uM | 156 |
| nortriptylene 0.5 uM | 2040 |
| nortriptylene 10 uM | 648 |
| No IL-1β | low |
| No IL-1β | low |
| No IL-1β | low |
| No IL-1β | 8 |

TABLE 3-continued (10% fetal calf serum-containing media)

| Sample | $PGE_2$ (pg/ml) |
|---|---|
| +IL-1β | 5800 |
| +IL-1β | 2760 |
| +IL-1β | 5630 |
| +IL-1β | 10970 |

TABLE 4

(5% fetal calf serum-containing media)

| Sample | $PGE_2$ (pg/ml) |
|---|---|
| No IL-1β | low |
| +IL-1β | 909 |
| celebrex 0.5 uM | low |
| celebrex 10 uM | low |
| rac-fluoxetine 0.5 uM | 22 |
| rac-fluoxetine 10 uM | low |
| nortriptylene 0.5 uM | 880 |
| nortriptylene 10 uM | 331 |
| No IL-1β | low |
| No IL-1β | low |
| No IL-1β | low |
| No IL-1β | low |
| +IL-1β | 1520 |
| +IL-1β | 1250 |
| +IL-1β | 1500 |
| +IL-1β | 3870 |

Surprisingly, these results indicate that enantiomerically pure R- and S-norfluoxetine exhibit substantially equipotent anti-inflammatory activity in vitro, whereas S-norfluoxetine is known to be approximately 20-fold more active than R-norfluoxetine in the inhibition of serotonin reuptake.

5.3. Example 3

Determination of $IC_{50}$ Values

The $IC_{50}$ values of enantiomerically pure R- and S-norfluoxetine were determined by incubation of the WI-38 cells with varying concentrations of the compounds in question (0.009, 0.019, 0.039, 0.078, 0.156, 0.3125, 0.625, 1.25, 2.5, 5, 10, and 20 μm). The $PGE_2$ produced for each concentration was plotted against the concentration of compound using the 6 safit 4.0 program (Erithacus software) and the $IC_{50}$ determined by fitting the data to the 4-parameter equation. From these tests, it was determined that the $IC_{50}$ of R-norfluoxetine is about 0.79 uM, and that of S-norfluoxetine is about 1.4 uM.

It is noteworthy that these values, especially that of R-norfluoxetine, fall within values that may be obtained in serum in humans. For example, the package insert for Prozac® states that serum levels of norfluoxetine range from 72 to 258 ng/ml (approximately 0.23 to 0.83 uM) after treatment for 30 days with 40 mg per day of fluoxetine.

While the invention has been described with respect to the particular embodiments, it will be apparent to those skilled in the art that various changes and modifications may be made without departing from the spirit and scope of the invention as defined in the claims. Such modifications are also intended to fall within the scope of the appended claims.

What is claimed is:

1. A method of treating inflammation in a patient which comprises administering to a patient in need of such treatment a therapeutically effective amount of norfluoxetine, or a pharmaceutically acceptable salt, solvate, hydrate, or clathrate thereof.

2. The method of claim 1 wherein the inflammation is local or systemic.

3. The method of claim 1, wherein the norfluoxetine is enantiomerically pure R- or S-norfluoxetine.

4. The method of claim 3 wherein the norfluoxetine is enantiomerically pure R-norfluoxetine.

5. The method of claim 1 which further comprises the administration of a second active ingredient to the patient, wherein said second active ingredient is an anti-inflammatory drug, an analgesic, a proton-pump inhibitor, or an uricosuric agent.

6. The method of claim 5 wherein the anti-inflammatory drug is a corticosteroid, an NSAID, a leukotriene inhibitor, a gold complex, or an antihistamine.

7. The method of claim 6, wherein the anti-inflammatory drug is an NSAID.

8. The method of claim 6, wherein the anti-inflammatory drug is an antihistamine.

9. The method of claim 1 wherein the therapeutically or prophylactically effective amount is from about 1 mg to about 500 mg per day.

10. The method of claim 9 wherein the therapeutically or prophylactically effective amount is from about 10 mg to about 300 mg per day.

11. The method of claim 10 wherein the therapeutically or prophylactically effective amount is from about 15 mg to about 200 mg per day.

12. The method of claim 11 wherein the therapeutically or prophylactically effective amount is from about 20 mg to about 100 mg per day.

13. The method of claim 1 wherein the administration is oral, mucosal, parenteral, or transdermal.

14. The method of claim 13 wherein the administration is oral.

* * * * *